United States Patent

Clemence et al.

[11] Patent Number: 5,182,282
[45] Date of Patent: Jan. 26, 1993

[54] 4-BENZYL-1H-INDOLE DERIVATIVES

[75] Inventors: Francois Clemence; Jacques Guillaume, both of Paris; Gilles Hamon, Le Raincy, all of France

[73] Assignee: Roussel Uclaf, Paris, France

[21] Appl. No.: 781,070

[22] Filed: Oct. 11, 1991

Related U.S. Application Data

[62] Division of Ser. No. 514,695, Apr. 26, 1990, Pat. No. 5,086,070.

[30] Foreign Application Priority Data

Apr. 28, 1989 [FR] France ................. 89 05650

[51] Int. Cl.$^5$ ................. A61K 31/495; C07D 403/02
[52] U.S. Cl. ................. 514/253; 514/232.5; 514/235.2; 514/323; 544/82; 544/143; 544/144; 544/313; 546/201
[58] Field of Search ................. 544/143, 144, 373, 82; 514/235.2, 232.5, 253

[56] References Cited

U.S. PATENT DOCUMENTS 4,808,609 2/1989 Clemence et al. ................. 514/415

Primary Examiner—Nicholas S. Rizzo
Assistant Examiner—Jyothsna Venkat
Attorney, Agent, or Firm—Bierman and Muserlian

[57] ABSTRACT

Novel 4-benzyl-1H-indoles of the formula

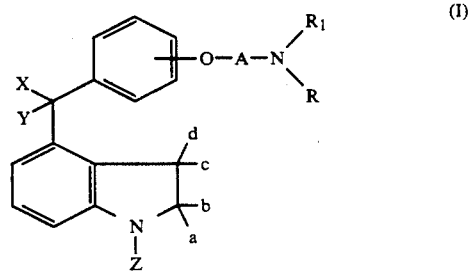

in all diastereoisomeric forms and mixtures thereof having anti-arhythmic activity.

19 Claims, No Drawings

4-BENZYL-1H-INDOLE DERIVATIVES

PRIOR APPLICATION

This application is a division of U.S. Pat. application Ser. No. 514,695, filed Apr. 26, 1990, now U.S. Pat. No. 5,086,070.

STATE OF THE ART

Related prior art references include U.S. Pat. Nos. 4,808,609 and No. 4,791,109.

OBJECTS OF THE INVENTION

It is an object of the invention to provide the novel compounds of formula I and their non-toxic, pharmaceutically acceptable acid addition salts and a novel process and novel intermediates for their preparation.

It is another object of the invention to provide novel anti-arhythmic compositions and a novel method of inducing anti-arhythmic activity in warm-blooded animals. These and other objects and advantages of the invention will become obvious from the following detailed description.

THE INVENTION

The novel 4-benzyl-1H-indoles of the invention are selected from the group consisting of all possible racemic or diastereoisomer forms of a 4-benzyl-1H-indole compound of the formula

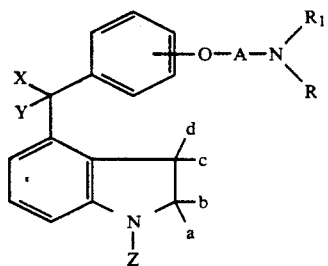

wherein $R_1$ and $R$ are individually selected from the group consisting of hydrogen, alkyl of 1 to 8 carbon atoms, alkenyl and alkynyl of 2 to 8 carbon atoms, cycloalkyl of 3 to 7 carbon atoms, cycloalkylalkyl of 4 to 12 carbon atoms, aralkyl of 7 to 12 carbon atoms, all optionally substituted with at least one member of the group consisting of halogen, alkyl and alkoxy of 1 to 5 carbon atoms, $-OH$, $-CF_3$, $CH_3S-$, $-NO_2$, $-NH_2$ and mono and dialkylamino of 1 to 4 alkyl carbon atoms or taken together with the nitrogen to which they are attached form a saturated or unsaturated heterocycle optionally containing a second heteroatom selected from the group consisting of $-O-$, $-N-$ and $-S-$ and optionally substituted with at least one member of the group consisting of alkyl of 1 to 5 carbon atoms, cycloalkyl of 3 to 7 carbon atoms, cycloalkylalkyl of 4 to 12 carbon atoms, phenyl, naphthyl, aralkyl and diaralkyl of 7 to 14 carbon atoms, all optionally substituted, A is

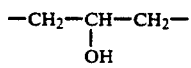

$-(CH_2)_n-$, n is 2,3,4 or 5, X and Y are both hydrogen or one is hydrogen and the other is selected from the group consisting of $-OH$, alkoxy and alkyl of 1 to 4 carbon atoms, or X and Y together form a member of the group consisting of $=O$, alkylidene of 1 to 4 carbon atoms and $=N-OR_5$, $R_5$ is hydrogen or alkyl of 1 to 4 carbon atoms, a, b, c and d are all hydrogen or a and b form $=O$ and c and d are hydrogen or one of a and b with one of c and d form a carbon-carbon bond and the others are both hydrogen, Z is selected from the group consisting of hydrogen, alkyl of 1 to 5 carbon atoms, alkenyl and alkynyl of 2 to 5 carbon atoms, cycloalkylalkyl of 4 to 12 carbon atoms and aralkyl of 7 to 14 carbon atoms, all optionally substituted and

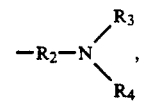

$R_2$ is alkylene of 2 to 5 carbon atoms, $R_3$ and $R_4$ are individually selected from the group consisting of hydrogen, alkyl of 1 to 5 carbon atoms, cycloalkyl of 3 to 7 carbon atoms, cycloalkylalkyl of 4 to 12 carbon atoms and aralkyl of 7 to 12 carbon atoms, all optionally substituted or taken together with the nitrogen to which they are attached form a saturated or unsaturated heterocycle optionally containing a second heteroatom selected from the group consisting of $-O-$, $-N-$ and $-S-$ and optionally substituted with at least one member of the group consisting of alkyl of 1 to 5 carbon atoms, cycloalkyl of 3 to 7 carbon atoms, cycloalkyl of 4 to 12 carbon atoms, phenyl, naphthyl and aralkyl and diaralkyl of 7 to 14 carbon atoms and their non-toxic, pharmaceutically acceptable acid addition salts.

Examples of alkyl of 1 to s carbon atoms are methyl, ethyl, n-propyl, isopropyl, butyl, sec.-butyl, isobutyl, tert.-butyl, pentyl, isopentyl, sec.-pentyl, tert.-pentyl and neopentyl and preferred examples of alkyl of 1 to 4 carbon atoms are methyl, ethyl, propyl, isopropyl, butyl, isobutyl, sec.-butyl and tertiary butyl.

When X or Y is alkyl of 1 to 4 carbon atoms, it preferably has the formula $-CH_2-R_a$ in which $R_a$ is alkyl chosen from methyl, ethyl, propyl and isopropyl that is to say linear or branched alkyls of 1 to 3 carbon atoms. Examples of alkenyl of 2 to 8 carbon atoms are vinyl, allyl, 1-propenyl, butenyl, pentenyl and hexenyl. Examples of alkynyl of 2 to 8 carbon atoms are preferably ethynyl, propargyl and butynyl.

Examples of alkylidene of 1 to 4 carbon atoms are preferably methylene, ethyldene, propylidene and butylidene. Examples of cycloalkyl of 3 to 7 carbon atoms are preferably cyclopropyl, cyclobutyl, cyclopentyl and cyclohexyl and examples of cycloalkylalkyl of 4 to 12 carbon atoms are preferably cyclopropylmethyl, cyclopropylethyl, cyclopropylpropyl, cyclobutylmethyl, cyclobutylethyl, ethylcyclobutylmethyl, cyclobutylpropyl, diisopropylcyclobutyl, cyclopentylmethyl, cyclopentylethyl cyclopentylpropyl, diisopropylcyclopentyl, cyclopentylbutyl, cyclopentylpentyl and methylcyclohexylpentyl.

Examples of aralkyl or diaralkyl of 7 to 14 carbon atoms are preferably benzyl, phenethyl, α-methylphenethyl, phenylpropyl, α-methyl-phenylpropyl, β-methyl phenylpropyl, phenylbutyl, diphenylmethyl or 1,1-diphenyl ethyl.

The optional substituents applied to the presence of the aforementioned group as well as to phenyl and naphthyl are preferably at least one substituent selected from the group consisting of halogen, alkyl or alkoxy of 1 to 5 carbon atoms, hydroxy, trifluoromethyl, methylthio, nitro, amino and monoalkylamino or dialkylamino. Halogen preferably is fluorine, chlorine or bromine and the alkoxy of 1 to 5 carbon atoms are preferably mothoxy, ethoxy, propoxy or tert.-butoxy. The monoalkylamino or dialkylamino are preferably alkyl of 1 to 5 carbon atoms such as methylamino, ethylamino, methylethylamino, dimethylamino, diethylamino or ethylpropylamino.

The saturated or unsaturated heterocycle which can be formed by R and $R_1$ or $R_3$ and $R_4$ with the nitrogen atom to Which they are respectively attached are preferably heteroycycle of 5 or 6 links able to contain a second heteroatom chosen from oxygen, nitrogen or sulfur atoms and most preferably pyrrolidinyl, imidazolidinyl, pyrazolidinyl, piperidinyl, morpholinyl, piperazinyl, methylpiperazinyl, ethylpiperazinyl or propylpiperazinyl.

Examples of the salts with mineral or organic acids are inorganic acids such as the salts formed with hydrochloric acid, hydrobromic acid, nitric acid, sulfuric acid and phosphoric acid and organic acids such as acetic acid, formic acid, propionic acid, malonic acid, maleic acid, fumaric acid, succinic acid, tartaric acid, citric acid, oxalic acid, glyoxylic acid, aspartic acid, alkanesulfonic acids such as methane- or ethanesulfonic acid, arylsulfonic acids such as benzene- or p-toleunesulfonic acid and arylcarboxylic acid carboxylic acids such as benzoic acid.

Among the preferred compounds of formula I are those wherein $R_1$ and R are individually selected from the group consisting of hydrogen, alkyl of 1 to 8 carbon atoms and alkenyl and alkynyl of 2 to 8 carbon atoms optionally substituted with hydroxy, cycloalkyl of 3 to 7 carbon atoms, cycloalkylalkyl of 4 to 7 carbon atoms and aralkyl of 7 to 14 carbon atoms containing 1 to 3 aryl substituents selected from the group consisting of —OH, halogen, alkyl and alkoxy of 1 to 5 carbon atoms, —$CF_3$, $CH_3$—S, —$NO_2$, —$NH_2$ and monoalkyl and dialkylamino or R and $R_1$ taken together with the nitrogen to which they are attached form a saturated or unsaturated heterocycle optionally containing a heteroatom of the group consisting of —O—, —S— and —NR'—, R' being selected the group consisting of hydrogen, alkyl of 1 to 5 carbon atoms, phenyl optionally substituted with 1 to 3 members of the group consisting of —OH, halogen, alkyl and alkoxy of 1 to 3 carbon atoms, —$CF_3$, $CH_3$—S, —$NO_2$, —$NH_2$ and mono and dialkylamino, naphthyl and aralkyl and diaralkyl of 7 to 14 carbon atoms optionally substituted with 1 to 3 aryl substituents selected from the group consisting of —OH, halogen, alkyl and alkoxy of 1 to 3 carbon atoms —$CF_3$, $CH_3S$—, —$NO_2$, —$NH_2$ and mono and dialkylamino and those wherein Z is selected from the group consisting of hydrogen, alkyl of 1 to 5 carbon atoms, alkenyl and alkynyl of 2 to 5 carbon atoms, cycloalkyl-alkyl of 4 to 7 carbon atoms, aralkyl of 7 to 14 carbon atoms optionally having 1 to 3 substituents selected from the group consisting of —OH, halogen, and alkyl and alkoxy of 1 to 5 carbon atoms and

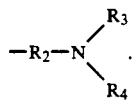

wherein $R_3$ and $R_4$ are individually selected from the group consisting of hydrogen and alkyl of 1 to 5 carbon atoms and $R_2$ is alkylene of 2 to 5 carbon atoms.

More preferred compounds of formula I are those wherein Z is hydrogen or alkyl of 1 to 4 carbon atoms, those wherein X and Y are both hydrogen or together form =O or alkylidene, those wherein R is hydrogen, $R_1$ is alkyl of 1 to 4 carbon atoms or cycloalkyl of 3 to 7 carbon atoms, those wherein $R_1$ and R together with the nitrogen form a heterocycle optionally containing a second nitrogen which can optionally be substituted with alkyl of 1 to 5 carbon atoms, those wherein A is $(CH_2)_n$— where n is 2 or 3 or is

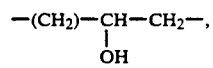

those where one of a and b together with one c and d form a carbon-carbon bond and the other two are hydrogen or a and b are =O and c and d are hydrogen and their non-toxic, pharmaceutically acceptable acid addition salts.

Specific preferred compounds of formula I are [2-[3-[(1,1-dimethylethyl)-amino]-2-hydroxypropoxy]-phenyl]-(1H-indol-4-yl) methanone;[2-[3-[(1,1-dimethylethyl)-amino]-propoxy]-phenyl]-(1H-indol-4-yl)-methanone; 1-[(1,1-dimethylethyl)-amino]-3-[2-[(1H-indol-4-yl)-methyl]-phenoxy]-2-propanol; (±) [2-[3-[1,1-dimethylethyl)-amino]-2-hydroxypropoxy]-phenyl]-(1-methyl-1H-indol-4-yl) methanone; 1,3-dihydro-4-[2-[3-(1,1-dimethylethyl)-amino]-2-hydroxypropoxy]-benzoyl]-2H-indol-2-one; (+) 3-[(1,1-dimethylethyl)-amino]-1-[[2-(1H-indol-4-yl)-ethenyl]-phenoxy]-2-propanol; N-(1,1-dimethylethyl)-3-[2-[1-(1H-indol-4-yl)-ethenyl]-phenoxy]propanamine; α[2-[3-[(1,1-dimethylethyl)-amino]-2-hydroxypropoxy]-phenyl-1H-indol-4-methanol and their non-toxic, pharmaceutically acceptable acid addition salts.

The novel process of the invention for the preparation of the compounds of formula I comprises reacting a compound of the formula

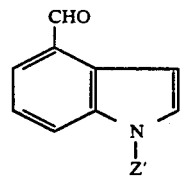

wherein Z' is Z other than hydrogen or protected reactive groups or protector group thereof with an organometallic compound of the formula

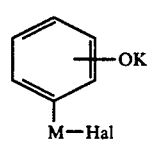

wherein K is a protector group of hydroxy, M is lithium or magnesium, Hal is halogen to obtain a product of the formula

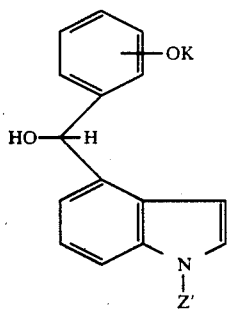

IV oxidizing the latter to obtain a product of the formula

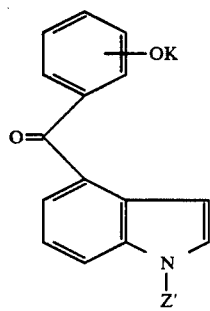

V selectively freeing the hydroxy group to obtain a product of the formula

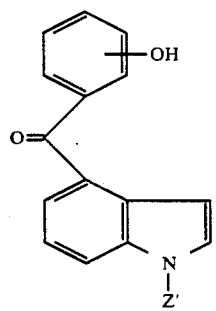

VI and optionally either the product of formula VI is subjected to a reduction of the oxo function to obtain a product of the formula

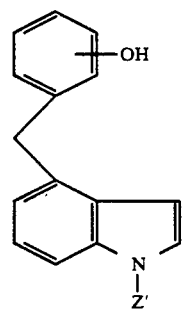

VII or the product of formula VI is subjected to the action of an organo-metallic reagent, then to the action of a dehydration agent to obtain a product of the formula

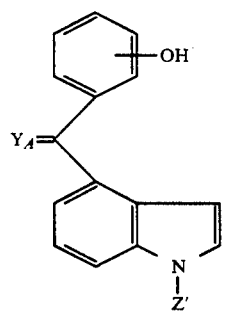

VIII wherein $Y_A$ is alkylidene of 1 to 4 carbon atoms, which product of formula VIII is optionally hydrogenated to obtain a product of the formula

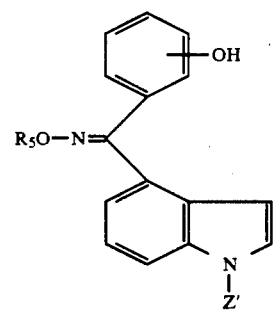

VIII' in which $Y_B$ is alkyl of 1 to 4 carbon atoms, or the product of formula VI is converted to the corresponding oxime of the formula

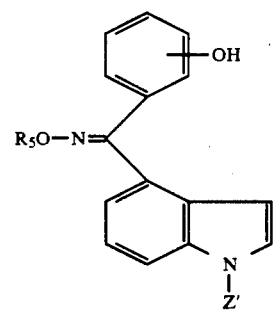

IX wherein $R_5$ has the meaning indicated previously, the products of formulae VI, VII, VIII, VIII' or IX are subjected to a condensation reaction on the hydroxy group either with a product of the formula

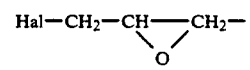

X to obtain a product of the formula

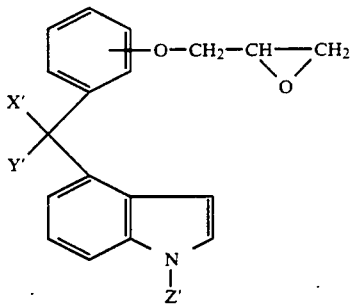

XI in which X' and Y' are hydrogen or together form an oxo, alkylidene or a =N—OR$_5$, or one is hydrogen and the other is alkyl of 1 to 4 carbon atoms, or with the product of the formula Hal—A'—Hal      XII in which A' is —(CH$_2$)$_n$ to obtain a product of the formula

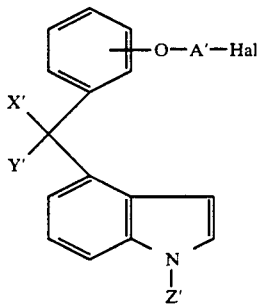

XIII in which A', Z', X' and Y' have the meaning given above, and the products of the formulae XI or XIII are subjected to an addition reaction with an amine of the formula

NH—(R)—(R$_1$)      XIV in which R and R have the meaning indicated above to obtain a product of the formula

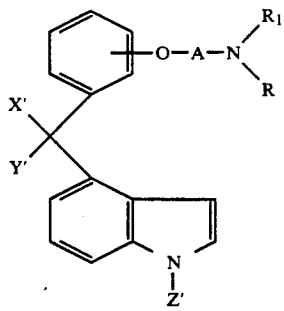

XV which are optionally subjected to one or more of the following reactions in any order:

a) optional detachment of Z' or the protector groups of Z' if necessary to obtain Z, b) reduction of the oxo formed by X' and Y' into an alcohol function, followed if necessary and if desired by an optional alkylation of the hydroxy function formed by X or Y to obtain the products of formula I in which X or Y is alkoxy, c) reduction of the double bond of the pyrrole nucleus of the indole radical to obtain the products of formula I in which a,b,c and d each are hydrogen, d) halogenation at beta position of the nitrogen atom on the pyrrole nucleus of the indole followed by a hydrolysis in an acid medium to obtain the products of formula I in which a and b form an oxo function, e) resolution of the racemic products by standard processes to obtain the optically active products, and salification, if desired, of the products of formula I to obtain the corresponding salts.

In the products of formula II, Z' can be a protector group of the nitrogen obtained by addition of a halide in the presence of a basic agent. In this case, preferably this protector group is a tosyl radical (4-methylbenzene sulfonyl) obtained by the addition of tosyl chloride in a basic medium such as 50% sodium hydroxide and tetrabutyl-ammonium hydrogenosulfate in the presence of benzene at ambient temperature for about 90 minutes.

The protector groups of the amino-N(R$_3$)(R$_4$) that Z contains, when at least one of R$_3$ or R$_4$ is a hydrogen atom, or also of an amino or monoalkylamino when it is a question of a substituent of an aralkyl, diaralkyl, phenyl or naphthyl as defined above, that the cycle formed, if appropriate, by R$_3$ or R$_4$, can carry for example acyl optionally substituted by one or more halogen such as chloroacetyl, dichloroacetyl or trichloroacetyl or trifluoroacetyl; alkoxy or cycloalkyloxycarbonyl group such as for example methoxycarbonyl or tert-butoxycarbonyl; aromatic aralkyl group such as for example benzyl.

The above list is not limitative and other examples of protector groups can be found in French Patent No. 2,499,995, the content of which is incorporated by way of reference into the present application.

In the product of formula III which is either an organolithium compound or an organomagnesium compound, the hydroxy radical protected by K can be an alkoxy such as methoxy, benzyloxy or also trimethylsilyloxy. The halogen that Hal is can be either chlorine or bromine.

The condensation reaction of the product of formula II or indole-4-carboxaldehyde derivative with the organometallic compound of formula III takes place, for example, in a solvent which can be THF (tetrahydrofuran) at a temperature of 0 to 5° C. for one hour. The alcohol of formula IV is subjected to an oxidation reaction for example in pyridinium chlorochromate or preferably in pyridinium dichromate in an inert solvent such as a halo- or polyhaloalkane and preferably methylene chloride (dichloromethane) for about 20 hours at ambient temperature.

The protected hydroxy group of the product of formula V can be freed selectively to keep the protector groups as defined above, by cleavage of the K protector to obtain the product of formula VI, for example in the presence of a LEWIS acid which can be boron tribromide or boron tribromide dimethylsulfide in dichloromethane at low temperature, or also, preferably, pyridinium hydrochloride at high temperature, preferably about 180° C.

The product of formula VI can be reduced at the oxo function to obtain the product of formula VII, for example by lithium in liquid ammonia or preferably by hydrazine hydrate in diethylene glycol in the presence of potassium hydroxide at a temperature of approximately 130° C. about 90 minutes. To obtain a product of formula VIII, the product of formula VI is reacted with an organometallic reagent such as methyl magnesium halide in an organic solvent and operating at reflux of this solvent, then to a dehydration reaction obtained for example by heating the reaction medium at 50° C. and acidifying it.

The product of formula VIII' can be obtained by catalytic hydrogenation in the presence of palladium of the product of formula VIII. The product of formula VI can be converted to an oxime of formula IX by standard methods such as condensation with hyroxylamine or a derivative of the formula $H_2N—OR_5$.

The products of formulae VI, VII, VIII, VIII' or IX can be subjected to an addition reaction on the hydroxy of the phenol by a halogented derivative of formula X or XII in which the halogen(s) can be either chlorine or bromine: either by a condensation reaction with the halogenated derivative of formula X such as epichlorhydrin in the presence of an alkaline agent such as sodium hydroxide, potassium hydroxide, sodium carbonate or preferably potassium carbonate at reflux of an organic solvent such as acetone or a dialkylketone such as methyl ethyl ketone or methyl isobutyl ketone for about 24 hours to obtain the products of formula XI or by a substitution reaction with the dihalogenated derivative of formula XII such as 1-bromo-3-chloro propane at reflux of a polar solvent which can be either an alcohol such as ethanol, an oxo derivative such as acetone or also DMF (dimethylformamide) and in the presence of a basic agent such as sodium or potassium carbonate to obtain the products of formula XIII.

The addition of the amine of formula XIV such as tert-butylamine on the compounds of formula XI or XIII is carried out at reflux for about 2 hours of a polar solvent which can be an alcohol such as ethanol or also DMF optionally in the presence of a basic agent such as sodium or potassium carbonate. The products of formula XV may or may not be products of formula 1. The products of formula XV constitute the products of formula I when Z' is not a protector group or does not carry a protector group. These products of formula XV can therefore be subjected, if necessary or if desired, to one or more of the following reactions in any order: a) optional detachment of Z' or the protector groups carried by Z' is necessary to obtain Z, for example by a saponification reaction with an agent such as sodium cyanide in the presence of DMSO (dimethylsulfoxide) at a temperature of about 100 C or preferably alcoholic potassium hydroxide b) reduction of the oxo function formed by X' and Y' into an alcohol function, for example by an alkali metal borohydride such as potassium tetraborohydride or preferably sodium tetraborohydride in an alcoholic medium such as methanol at reflux, or by lithium aluminium hydride in THF or ether.

c) optional alkylation of the hydroxyl which can be one of X' or Y' is carried out preferably by the action of a reactive derivative of alkyl, for example methyl sulfated) reduction of the double bond of the pyrrole nucleus of the indole by standard processes to obtain the products of formula I in which a, b, c and d each are hydrogen. This reduction can be obtained: by catalytic hydrogenation in the presence of platinium under slight hydrogen pressure, by diborane in a polar solvent such as THF followed by treatment in a solution of sodium or potassium alcoholate in an alcohol, preferably sodium methylate in methanol, or by diborane complexes which can be an aminoborane such as pyridineborane or trimethylaminoborane in an alcohol such as ethanol or also dioxane in the presence of hydrochloric acid. e) halogenation at the beta position of the nitrogen on the pyrrole nucleus of the indole by standard processes, followed by hydrolysis in an acid medium to obtain the products of formula I in which a and b form an oxo: the halogenation can be obtained with an N- halo-succinimide such as N-chlorosuccinimide (NCS) or N- bromosuccinimide in an organic solvent such as dioxane or acetic acid and the hydrolysis can be effected in a medium of hydrochloric acid or of aqueous phosphoric acid. f) resolution of the racemic products by standard processes to obtain the optically active products and salification also by known methods of the products of formula I to obtain the corresponding salts.

Among these salification methods are those which use the basic character of the products of formula I. Thus, the addition salts of the derivatives of formula I can be advantageously prepared by reacting in approximately stoichiometric proportions a mineral or organic acid with the said derivative of formula I and the salts can be prepared without isolating the corresponding bases.

The products of formula II are known or can be prepared as indicated, notably, in J. Org. Chem. (1980), Vol. 45, p. 3350 and subsequent, or also are new and can be prepared by the addition of a halide of the formula Hal—Z'  XVI in which Z' has the above meaning and Hal preferably is iodine to the known product of formula XVII or (1H}-indole-4-carboxaldehyde:

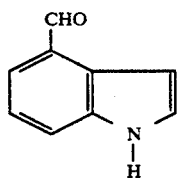

XVII in a two-phase mixture of alkyl halide such as dichloromethane in an alkaline medium, for example aqueous sodium hydroxide and a quaternary ammonium salt such as tetrabutyl ammonium hydrogenosulfate. An example of this preparation is given in the experimental part.

The organo-metallic products of formula III are known products which can be prepared, for example, from 1-bromo-4-methoxy-benzene or commercially available 4-bromo-anisole on to which magnesium is added in the presence of THF.

The novel antiarhythmic compositions of the invention are comprised of an anti-arhythmically effective amount of at least one compound of formula I and its non-toxic, pharmaceutically acceptable acid addition salts and an inert pharmaceutical carrier. The compositions may be in the form of tablets, dragees, capsules, granules, suppositories or injectable solutions or suspensions.

Examples of suitable excipients or pharmaceutical carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

The compositions have a remarkable anti-arhythmic activity as well as blocking properties for the slow calcisodic canals (anticalcic property). Some of the compounds also possess properties for the anti-aggregation of blood-platelets and beta-blocking properties. The compositions are therefore useful in the treatment of cardiac insufficiency and arhythmia, migraines and angina pectoris in all its forms, both in the case of spastic angina and unstable angina. The compositions can also be used in anti-thrombotic treatment.

The novel method of the invention of inducing anti-arhythmic activity in warm-blooded animals, including humans, comprises administering to warm-blooded animals an anti-arhythmically effective amount of at least one compound of formula I and its non-toxic, pharmaceutically acceptable acid addition salts. The compounds may be administered orally, rectally or parenterally and the usual daily dose is 0.8 to 16 mg/kg depending on the condition treated, the specific compound and the method of administration. For example, it can be 5 to 10 mg/kg with the compound of example 4 for treating cardiac rhythmic desorders by oral route in human.

The novel intermediate compounds of the invention are those of formulae II, IV, V, VI, VII, VIII, VIII', IX, XI, and XIII as defined above.

In the following examples there are described several preferred embodiments to illustrate the invention. However, it could be understood that the invention is not intended to he limited to the specific embodiments.

EXAMPLE 1

Neutral fumarate of
[4-[3-[(1,1-d1methyl-ethyl)-amino]-propoxy]phenyl]-
(1H-indol-4-yl )-methanone

STEP A:

1-[(4-methyl-phenyl)-sulfonyl]-1H-indol-4-carboxaldehyde 150 ml of 50% sodium hydroxide, 4.75 g of tetrabutylammonium hydrogenosulfate and 30.24 g of p-toluene sulfonyl chloride were added to a suspension of 20 g of indole 4carboxaldehyde in 600 ml of benzene and the mixture was stirred or 90 minutes at ambient temperature. After decanting and extracting with benzene, the extracts were washed with water, dried and evaporated to dryness under reduced pressure. The 42.1 g of residue were dissolved in 210 ml of benzene at reflux, and the solution was allowed to cool to ambient temperature over 16 hours, then separated to obtain 23.96 g of the desired product melting at 144 to 146° C. The product was used as is for the following step.

| IR Spectrum (CHCl$_3$) | |
|---|---|
| Absence of NH | |
| C=O aldehyde | 1691 cm$^{-1}$ |
| C—H aldehyde | 2740 cm$^{-1}$ |

STEP B:

λ-(4-methoxy-phenyl)-1-[(4-methyl-phenyl)-sulfonyl]-1H-indole-4-methanol

A solution of 60 g of the product of Step A in 600 ml of tetrahydrofuran was added slowly at 0 to +5° C. to 226 ml of a solution of 4-bromo anisole magnesium compound in tetrahydrofuran titrating 1.77 M/l. The mixture was stirred for one hour at 0 to +5° C. and after 250 ml of a saturated solution of ammonium chloride were added, the temperature was maintained at 5° C. Extraction was done with methylene chloride and the extracts were evaporated to dryness under reduced pressure to obtain 114 g of product which was made into a paste in 150 ml of isopropyl ether to obtain 78.2 g of the desired product melting at 90° C. An analytical sample was obtained by crystallizing 1 g of the product from 10 ml of isopropanol to obtain 0.93 g of product melting at 90° C.

| IR Spectrum | |
|---|---|
| Absence of C=O | |
| OH at 3601 cm$^{-1}$ | |
| | (1612 cm$^{-1}$ |
| C=C | )1599 cm$^{-1}$ |
| aromatic | (1586 cm$^{-1}$ |
| | (1528 cm$^{-1}$ |
| | )1511 cm$^{-1}$ |
| | (1495 cm$^{-1}$ |

STEP C: (4-methoxy-phenyl)-[1-[(4-methyl phenyl)-sulfonyl[1H-indol-4-yl]-methanone 15.6 g of siliporite NK 30 and 105.4 8 of pyridinium dichromate were added to a solution of 78 g of the alcohol of Step B in 1500 ml of methylene chloride and the mixture was stirred for 20 hours at ambient temperature, filtered and concentrated to dryness under reduced pressure. The residue was chromatographed on silica (eluant: methylene chloride) to obtain 71.9 g of the desired product melting at 135° C. which was used as is for the following step.

| IR Spectrum | |
|---|---|
| C=O | 1646 cm$^{-1}$ |
| C=C and aromatic: | 1600, 1573, 1510, 1495 cm$^{-1}$ |

STEP D: (1H-indol-4-yl) (4-hydroxy-phenyl) methanone

A solution of 56.1 8 of the product of Step C, 66.16 g of sodium cyanide and 370 ml of dimethylsulfoxide was heated for 16 hours at 140° C. and then the solution was allowed to return to ambient temperature. 1500 ml of 2N hydrochloric acid were added and extraction was done with sulfuric ether. The extracts were concentrated to dryness under reduced pressure and the 70.4 g residue were chromatographed on silica (eluant: methylene chloride-ethyl acetate (85-15) to obtain 20.1 g of the desired product melting at 177° C. which was used as is for the following step After chromatography on silica of 5.5 g of the above product (eluant: ethyl acetate-n-hexane (4-6)) and crystallization of the residue from ethyl acetate-n-hexane, 3.96 g of pure product melting at 177° C. were obtained.

Analysis: C$_{15}$H$_{11}$NO$_2$; Calculated: %C 75.94; %11 4.67; %N 5.9; Found: 75.7; 4.6; 5.8;

STEP E:

[4-(3-chloropropoxy)-phenyl]-(1H-Indol-4-yl)-methanone

A mixture of 5.93 g of the product of Step D, 6.91 g of potassium carbonate, 150 ml of acetone and 9.84 g of 1-bromo-3-chloro propane was stirred at reflux for 4 hours 30 minutes and the mixture was allowed to return to ambient temperature and filtered. The filtrate was washed with acetone and concentrated to dryness under reduced pressure. The 14.2 g of residue were chromatographed on silica (eluant: methylene chloride) to obtain 7.8 g of the desired product melting at 86° C., which was used as is for the following step.

| IR Spectrum | |
|---|---|
| No OH | |
| NH indole | 3479 cm$^{-1}$ |
| >C=O | 1640 cm$^{-1}$ |
| aromatic: | 1601, 1575, 1509 cm$^{-1}$ |

STEP F: [4-[3-[(1 1-dimethyl ethyl)-amino]-propoxy]-phenyl]-(1H-indol-4-yl]-methanone A mixture of 7.75 8 of the product of Step E, 6.83 g of potassium carbonate, 25.8 ml of tertbutylamine and 150 ml of ethanol was heated at 140° C. for 48 hours in an autoclave. After filtering, the filtrate was brought to dryness under reduced pressure and the 11.7 g of residue were chromatographed on silica (eluant: ethyl acetate-triethylamine (95-5)) to obtain 6.32 g of the desired product.

STEP G: Neutral fumarate of [4-[3-[(1,1-dimethyl-ethyl)-amino-propoxy]-phenyl]-(1H-indol-4-yl) methanone 5.45 g of the product of Step F were dissolved in 60 ml of ethanol and the solution was filtered A solution of 1.8 g of fumaric acid in 40 ml of ethanol was added and the resultant mixture was ice-cooled. 4.24 g of crystallized product were separated off which was purified by hot and cold crystallization from 600 ml of ethanol. Filtration was carried out and the filtrate was concentrated to half volume, ice-cooled, separated, rinsed with ether and dried at 80° C. under reduced pressure to obtain 3.62 g of the pure product melting at 210° C.

Analysis: 2[C$_{22}$H$_{26}$N$_2$O$_2$]C$_4$H$_4$O$_4$; Calculated %C 70.56; %H 6.91; %N 6.86; Found: 70.50; 6.90; 6.90;

EXAMPLE 2

Neutral fumarate of [4-[3[(1,1-dimethyl ethyl)-amino]-2-hydroxy propoxy]-phenyl]-(1H-indol-4-yl) methanone STEP A:
(1H-indol-4-yl)-[4-[(2-oxiranyl)-methoxy]-phenyl]methanone A mixture of 2.37 g of the product of Step D of Example 1, 2.76 g of potassium carbonate, 1.18 ml of epichlorhydrin and 40 ml of acetone was stirred at reflux for 3 hours and then 1.18 ml of epichlorhydrin were added. The mixture was stirred at reflux for another 5 hours and then 1.18 g of epichlorhydrin were added. The mixture was stirred at reflux and after 24 hours under reflux, the mixture was filtered. The filtrate was evaporated to dryness under reduced pressure and the 5.34 g of residue were chromatographed on silica (eluant: ethyl acetate-hexane (1-1)) to obtain 2.82 g of the desired product melting at 96° C.

| IR Spectrum | |
|---|---|
| NH indole | 3480 cm$^{-1}$ |
| ketone | 1640 cm$^{-1}$ |

| -continued | |
|---|---|
| IR Spectrum | |
| aromatics | 1600, 1576, 1509, 1497 cm$^{-1}$ |

STEP B: [4-[3-[(1,1-dimethyl ethyl)-amino]-2-hydroxy propoxy]-phenyl]-(1H-indol-4-yl) methanone A solution of 4.65 g of the product of Step A, 100 ml of ethanol and 9.94 ml of tert-butylamine was stirred at reflux for 2 hours and the solution was distilled to dryness. The 6.83 g of residue were chromatographed on silica (eluant: ethyl acetate triethylamine (9-1)) to obtain 4.77 g of the desired product.

STEP C: Neutral fumarate of [4-[3-(1,1-dimethyl ethyl)-amino]-2-hydroxy-propoxy-phenyl]-(1H-indol-4-yl) methanone Using the procedure of Step G of Example 1, 4.6 g of the product of Step B and 1.46 g of fumaric acid were reacted to obtain 3.4 g of the expected product melting at 210° C.

Analysis: 2[C$_{22}$H$_{26}$N$_2$O$_3$]C$_4$H$_4$O$_4$; Calculated: %C 67.9; %H 6.65; %N 6.6; Found: 67.2; 6.6; 6.2;

EXAMPLE 3

[2-[3-[(1,1-dimethyl ethyl)-amino-propoxy]-phenyl]-(1H-indol -4-yl) methanone benzoate STEP A:
4-hydroxy-(2-methoxy-phenyl)-methyl]-1-[(4-methyl phenyl)-sulfonyl]-1H-indole Using the procedure of Step B of Example 1, 80 g of the product of Step A of Example 1 and 207 ml of a solution of 2-bromo anisole magnesium compound in tetrahydrofuran titrating 2.28 M/l were reacted to obtain 109 g of the expected product which was used as is for the following step.

| IR Spectrum | |
|---|---|
| Absence of |  |
| OH at | 3600 cm$^{-1}$ |
| aromatics: | 1600, 1589, 1491, 1484 cm$^{-1}$ |
| SO$_2$ | 1773, 1178 cm$^{-1}$ |

STEP B: 4-(2-methoxy benzoyl)-1-(4-methyl-phenyl)-sulfonyl]-1H-indole

Using the procedure of Step C of Example 1, 108.9 g of the alcohol of Step A and 150.8 g of pyridinium dichromate were reacted to obtain 101.4 g of the desired product melting at 154° C. which was used as is for the following step.

| IR Spectrum | |
|---|---|
| No OH | |
| >C=O | 1657 cm$^{-1}$ |
| C=C and aromatics | 1599, 1580, 1521, 1488 cm$^{-1}$ |

STEP C:
4-(2-hydroxy-benzoyl)-1-(4-methyl-phenyl)-sulfonyl]-1H-indole

A mixture of 85 g of the product of Step B and 600 g of pyridine hydrochloride was heated at 180° C. for 4 hours and the mixture was cooled to 80° C. 700 ml of a saturated solution of sodium carbonate were added followed by extraction with ethyl acetate. The extracts were washed twice with 300 ml of N hydrochloric acid and then with water, dried and evaporated to dryness under reduced pressure. The 100.3 g of residue were chromatographed on silica (eluant: methylene chloride - hexane (8-2)) to obtain 78.8 g of the expected product which was used as is for the following step and melted at 110° C.

| IR Spectrum | |
|---|---|
| General absorption of the chelated —OH type | |
| >C=O | 1626 cm$^{-1}$ |
| C=C + aromatics | 1606, 1594, 1583, 1524, 1485 cm$^{-1}$ |

STEP D: (2-hydroxy-phenyl) (1H-indol-4-yl) methanone

A solution of 84.2 g of the product of Step C and 850 ml of 10% ethanolic potassium hydroxide was stirred at reflux for one hour and the methanol was evaporated off. The residue was taken up in a saturated aqueous solution of sodium chloride and extraction was done with ethyl acetate. The extracts were washed with water, dried and evaporated to dryness. The 63.8 g of residue were chromato-graphed on silica to obtain 49.6 g of product which was made into a paste in 150 ml of ethyl ether to obtain 40.9 g of the desired product melting at 165° C.

| IR Spectrum | |
|---|---|
| NH indole | 3479 cm$^{-1}$ |
| General absorption of the chelated —OH type | |
| >C=O | 1626 cm$^{-1}$ |
| aromatics | 1613, 1598, 1575, 1503, 1425 cm$^{-1}$ |

STEP E: [2-(3-chloro propoxy)-phenyl] (1H-Indol-4-yl) methanone

Using the procedure of Step E of Example 1, 10,9 g of the product of Step D and 18.17 ml of 1-bromo-3-chloro propane were reacted to obtain after chromatography on silica (eluant: methylene chloride - hexane (75-25]), 14.4 g of the desired product melting at 94° C., which was used as is for the following step.

| IR Spectrum | |
|---|---|
| C=O | 1648 cm$^{-1}$ |
| NH indole | 3479 cm$^{-1}$ |
| aromatics | 1609, 1599, 1581, 1571, 1489 cm$^{-1}$ |

STEP F: [2-[3-[(1,1-dimethyl-ethyl)-amino]-propoxy]-phenyl-(1H-indol-4-yl) methanone Using the procedure of Step F of Example 1, 14.3 g of the product of Step E were reacted to obtain 12.12 of the expected product melting at 130° C.

| IR Spectrum | |
|---|---|
| NH indole | 3479 cm$^{-1}$ |
| >C=O | 1649 cm$^{-1}$ |
| aromatics and conjugated: | 1609, 1599, 1581, 1572, 1488 cm$^{-1}$ |

STEP G: [2-[3-[(1,1-dimethyl ethyl)-amino]-propoxy]-phenyl](1H-indol-4-yl) methanone benzoate Using the procedure of Step G of Example 1, 3.0 g of the product of Step F, 1.05 g of benzoic acid were reacted to obtain 3.42 g of the product melting at 162° C., which was crystallized from isopropanol to obtain 2.73 g of the desired pure product melting at 162° C.

Analysis: $C_{22}H_{26}N_2O_2$, $C_7H_6O_2$; Calculated %C 73.71; %H 6.82; %N 5.93; Found: 73.7; 6.9; 5.9;

EXAMPLE 4

Neutral fumarate of [2-[3-(1,1-dimethyl ethyl)-amino]-2-hydroxy propoxy-phenyl]-(1H-indol-4-yl) methanone

STEP A: (1H-indol-4-yl)-[2-[(2-oxiranyl)-methoxy]-phenyl]methanone

Using the procedure of Step A of Example 2, 10.9 g of the product of Step D of Example 3 and 3 times 18 ml of epichlor hydrin were reacted to obtain 12.3 g of the desired product which was used as is for the next step.

| IR Spectrum | |
|---|---|
| NH indole | 3479 cm$^{-1}$ |
| >C=O | 1649 cm$^{-1}$ |
| aromatics | 1609, 1600, 1581, 1571 cm$^{-1}$ |

STEP B: 2-[3-[(1,1-dimethyl ethyl)-amino]-2-hydroxy-propoxy]-phenyl](1H-indol-4-yl) methanone Using the procedure of Step B of Example 2, 12.3 g of the product of Step A were reacted to obtain 12.45 g of the desired product melting at 130° C. which was used as is for the following step.

STEP C: Neutral fumarate of [2-[3-[(1,1-dimethyl ethyl)-amino]-2-hydroxy-propoxy]-phenyl]-(1H-indol-4-yl) methanone Using the procedure of Step G of Example 1, 3.0 g of the product of Step B and 1.19 g of fumaric acid in ethanol were reacted to obtain 2.05 g of the desired product melting at 245° C.

Analysis: $[C_{22}H_{26}N_2O_3]_2$, $C_4H_4O_4$; Calculated: %C 67.91; %H 6.65; %N 6.6; Found: 67.8; 6.5; 6.4;

EXAMPLE 5

1-[1,1-dimethyl-ethyl)-amino]-3-[2-[(1H-indol-4-yl)-methyl]-phenoxy-2-propanol

STEP A: 2-[(1H-indol-4-yl)-methyl]-phenol

A mixture of 22.74 g of the product of Step D of Example 3, 49.4 ml of hydrazine monohydrate, 96 ml of diethylene glycol and 38.4 ml of 38% caustic potassium hydroxide was stirred for 30 minutes at 140° C. and after the mixture was heated to 210° C., the water and hydrazine hydrate were distilled off. Stirring was continued for one hour at 210° C. and the mixture was allowed to return to ambient temperature and poured into 300 ml of a saturated aqueous solution of sodium chloride. Extraction took place with ethyl acetate and the extracts were evaporated to dryness under reduced pressure. The residue was chromatographed on silica (eluant: methylene chloride) to obtain 20.55 g of the desired product melting at 139° C. which was used as is for the following step.

| IR Spectrum | |
|---|---|
| NH indole | 3480 cm$^{-1}$ |
| OH + associated | 3598 cm$^{-1}$ |
| aromatic type bands: | 1617, 1585, 1489 cm$^{-1}$ |
| 2-alkylphenol | |
| other aromatic: | 1501 cm$^{-1}$ |

STEP B: 4-[[2-[(2-oxiranyl)-methoxy]-phenyl]-methyl]-1H-indole

Using the procedure of Step A of Example 2, 10.0 g of the product of Step A and 3 times 17.56 ml of epichlorhydrin were reacted to obtain 12.5 g of the desired product melting at 78° C. which was used as is for the following step.

| IR Spectrum | |
|---|---|
| No OH | |
| =C—NH— | 3482 cm$^{-1}$ |
| aromatics | 1611, 1600, 1587, 1492 cm$^{-1}$ |

STEP C: 1-[(1,1-dimethyl-ethyl)-amino]-3-2-(1H-indol-4-yl)-methyl]-phenoxy]-2-propanol Using the procedure of Step B of Example 2, 13.06 g of the product of Step B wore reacted to obtain 16.45 g of the desired product which was used as is for the following step.

STEP D: 1-[(1,1-dimethyl ethyl)-amino]-3-[2-(1H-indol-4-yl)-methyl]-phenoxy]-2-propanol benzoate.

Using the procedure of Step G of Example 3, 16.3 g of the product of Step C and 5.65 g of the benzoic acid were reacted to obtain 8.29 g of the desired product melting at 195° C. (ethanol).
Analysis: $C_{22}H_{28}N_2O \cdot C_7O_2H_6$
Calculated: %C 73.39; %H 7.22; %N 5.9; Found: 73.0; 7.3; 5.8

EXAMPLE 6

N(1,1-dimethyl ethyl)-3-[2-[(1H-indol-4-yl)-methyl]-phenoxy]-propanamine benzoate

STEP A: 4-[[2-(3-chloro propoxy)-phenyl]-methyl]1H-indole

Using the procedure of Step E of Example 1, 8.0 g of the product of Step A of Example 5 were reacted to obtain after chromatography on silica (eluant: methylene chloride-hexane (1-1)), 10.8 g of the desired product melting at 75° C. which was used as is for the following step.

| IR Spectrum | |
|---|---|
| No OH | |
| =C—NH— type indole | 3484 cm$^{-1}$ |
| C=C and aromatics: | 1612, 1600, 1588, 1492 cm$^{-1}$ |

STEP B: N-(1,1-dimethyl ethyl)-3-[2-[(1H-indol-4-yl)-methyl]-phenoxy]-propanamine Using the procedure of Step F of Example 1, 10.55 g of the product of Step A were reacted to obtain 8.65 g of the desired product melting at 96° C. which was used as is for the following step.

STEP C: N-(1,1-dimethyl ethyl)-3-[2-[(1H-indol-4-yl)-methyl]-phenoxy]-propanamine benzoate Using the procedure of Step G of Example 3, 8.12 g of the product of Step 8 and 2.95 g of benzoic acid were reacted to obtain 7.42 g of the desired product melting at 183° C. after crystallization from ethanol.

| Analysis: $C_{22}H_{28}N_2O \cdot C_7H_6O_2$ | | | |
|---|---|---|---|
| Calculated: | % C 75.95 | % H 7.47 | % N 6.11 |
| Found: | 76.1 | 7.5 | 5.8 |

EXAMPLE 7

α-[2-[3-[(1,1-dimethyl ethyl)-amino]-propoxy]-phenyl]-1H-indol-4-methanol benzoate

STEP A: α-[2-[3-[(1,1-dimethyl ethyl)-amino-propoxy]-phenyl]-1H-indole-4-methanol A mixture of 5.25 g of the product of Step F of Example 3, 70 ml of normal butanol and 1.7 g of sodium borohydride was stirred at reflux for one hour and the mixture was cooled. 200 ml of a saturated solution of sodium carbonate were added and extraction was carried out with an ethyl acetate-tetrahydrofuran mixture. The extracts were evaporated to dryness under reduced pressure and after chromatography on silica (eluant- :ethyl acetate-triethylamine (95-5)), 5.0 g of product melting at 205° C. were obtained. 4.3 g of the product were crystallized from 580 ml of acetonitrile to obtain 3.78 g of the desired product melting at 205° C.

| IR Spectrum |
| --- |
| Absence of \C=O / |
| complex absorptions NH/OH region<br>C=C and aromatics: 1602, 1590, 1496 cm$^{-1}$ |

Analysis: $C_{22}H_{28}N_2O_2$; Calculated: %C 74.97; %H 8.00; %N 7.95; Found: 75.0; 7.9; 8.2;

STEP B: α-[2[3-[(1,1-dimethyl ethyl)-amino]-propoxy]-phenyl]-1H-indole-4-methanol benzoate A solution of 0.745 g of benzoic acid in 11 ml of ethyl acetate was added at 70° C. to a mixture of 2.15 g of product of Step A and 400 ml of ethyl acetate. The solution obtained was filtered hot and cooled to obtain 2.62 g of the desired product melting at 185° C.

Analysis: $C_{22}H_{28}N_2O_2$, $C_7H_6O_2$; Calculated: %C 73.39; %H 7.22; %N 5.90; Found: 73.1; 7.3; 5.8.

EXAMPLE 8

α-[2-[3-[(1,1-dimethyl ethyl)-amino]-2-hydroxy-propoxy]-phenyl]-1H-indole-4-methanol benzoate STEP A: α-[2-[3-[(1,1-dimethyl ethyl)-amino]-2-hydroxy-propoxy]-phenyl]-1H-indole-4-methanol Using the procedure of Step A of Example 7, 6.9 g of the product of Step B of Example 4 were reacted to obtain after extracting with ethyl acetate and concentration to dryness and chromatography on silica (eluant: ethyl acetate-triethylamine (95-05)), 1.71 g of isomer A and 4.4 g of a mixture isomers A and B of the desired product. The mixture was chromatographed on silica (eluant: ethyl acetate - triethylamine - methanol (80-15-5)) to obtain a total of 3.29 g of isomer A melting at 205° C. and 2.51 g of isomer B which was chromatographed again to obtain 1.6 g of isomer B which can be used for the following example.

STEP B:
α-[2-[3-[(1,1-dimethylethyl)-amino]-2-hydroxy propoxy]-phenyl]-1H-indole-4-methanol benzoate (Isomer A)

3.29 g of isomer A of Step A were crystallized from 400 ml of acetonitrile to obtain 2.66 B of the product melting at 205° C. 2.6 g of crystallized isomer A were dissolved in 300 ml of ethyl acetate and 0.86 g of benzoic acid in solution in 30 ml of ethyl acetate were added, followed by filtering, ice-cooling for 12 hours, and separating to obtain 3 g of the desired product melting at 191° C.

Analysis: $C_{22}H_{28}N_2O_3$, $C_7H_6O_2$1 Calculated: %C 71.00; %H 6.98; %N 5.71; Found: 70.9; 7.1; 5.6.

EXAMPLE 9

α-[2-[3-[1,1-dimethyl ethyl)-amino]-2-hydroxy-propoxy]-phenyl]-1H-indole-4-methanol benzoate (Isomer B)

A solution of 0.41 g of benzoic acid in 10 ml of ethyl acetate was added to a solution of 1.25 g of isomer B (obtained in Step A of Example 8) in 50 ml of ethyl acetate to obtain 1.1 g of the expected product which was crystallized from 200 ml of acetonitrile to obtain 0.95 g of the desired product melting at 196° C.

Analysis: $C_{22}H_{28}N_2O_3$. $C_7H_6O_2$; Calculated: %C 71.00; %H 6.98; %N 5.71; Found: 70.9; 7.1; 5.9.

EXAMPLE 10

(±) [2-[3-[(1,1-dimethyl ethyl)-amino-2-hydroxy-propoxy]-phenyl](1-methyl-1H-indol-4-yl) methanone and its benzoate STEP A: 1-methyl-1H-indol-4-carboxaldehyde 34 g of indol 4-carboxaldehyde in 800 ml of methylene chloride were mixed for 4 hours at ambient temperature with 79.5 g of tetrabutyl ammonium hydrogen sulfate and 16.04 ml of methyl iodide in 400 ml of 5N sodium hydroxide and 300 ml of methylene chloride were added, followed by decanting and extraction was effected with methylene chloride. The organic phase was washed with a saturated aqueous solution of sodium chloride, dried and concentrated to dryness. Tho residue was chromatographed on silica (eluant: methylene chloride) to obtain 36.8 g of the expected product melting at <40° C.

STEP B:
α-(2-methoxyphenyl)-1-methyl-1H-indol-4-methanol

Using the procedure of Step B of Example 1, 36.8 g of the product of Step A and 104 ml of a solution of 2-bromo anisole magnesium compound in tetrahydrofuran titrating 1.94N were reacted. Extraction was carried out with ethyl acetate and the extracts were washed with salt water and brought to dryness. The residue was chromatographed on silica (eluant: methylene chloride) to obtain 46.S B of the expected product melting at 95° C.

STEP C: (2-methoxyphenyl)-(1-methyl-1H-indol-4-yl) methanone

Using the procedure of Step C of Example 1, 43.7 g of the alcohol of Step B and 92.4 g of pyridinium dichromate were reacted to obtain 30.1 g of the expected product melting at 74° C. which was used as is for the following step.

STEP D: (2-hydroxyphenyl)-(1-methyl-1H-Indol-4-yl) methanone

Using the procedure of Step C of Example 3, 29.9 g of the product of Step C and 300 g of pyridine hydrochloride were reacted to obtain using methylene chloride as eluant for the chromatography 17.2 g of the expected product melting at 80° C. which was used as is for the following step.

STEP E: (1-methyl-1H-indol-4-yl) [2-(2-oxiranylmethoxy)-phenyl]methanone

Using the procedure of Step A of Example 3, 3 g of the product of Step D, 6.6 of potassium carbonate and 4.7 ml of epichlorhydrin were added in 5 stages. After a total of 48 hours at reflux, filtration was carried out. The filtrate was concentrated to dryness under reduced pressure and the residue was chromatographed as indicated in Example 2 to obtain 3.7 g of the expected product.

| IR Spectrum | |
| --- | --- |
| C=O | 1650 cm$^{-1}$ |

-continued

| IR Spectrum | |
|---|---|
| aromatics | 1599, 1581, 1567, 1508, 1481 cm$^{-1}$ |

STEP F: (±)
[2-[3-[(1,1-dimethylethyl)-amino]-2-hydroxypropoxy]-phenyl](1-methyl-1H-indol-4-yl)methanone and its benzoate A solution of 3.7 g of the product of Step E, 80 ml of ethanol and 7.5 ml of tertbutylamine was stirred at reflux for 3 hours and 30 minutes and the solution was distilled to dryness The residue was chromatographed on silica (eluant: ethyl acetate - triethylamine 95-5) to obtain 3.82 g of the desired product in the form of its base. 3.80 g of the base were dissolved in 50 ml of ethanol and then a solution of 1.22 g of benzoic acid in 12 ml of ethanol was added. The mixture was ice-cooled for 12 hours, separated, washed with ethanol and dried at 80° C. under reduced pressure to obtain 4.05 g of the benzoate which after crystallization from ethanol melted at 166° C.

Analysis: $C_{23}H_{28}N_2O_3$. $C_7H_{16}O_2$; Calculated: %C 71.69 %H 6.82 %N 5.57; Found: 71.7; 6.8; 5.5.

EXAMPLE 11

(±)-
1-[(1,1-dimethylethyl)-amino]-3-[2-[(1-methyl-1H-indol-4-yl)-methyl]-phenoxy]-2-propanol and its benzoate STEP A: 2-[(1-methyl-1H-indol-4-yl)-methyl]-phenol Using the procedure of Step A of Example 5, 2.6 g of the product of Step D of Example 10, 5.33 ml of hydrazine hydrate, 10 ml of diethylene glycol and 4 ml of 38% caustic sodium hydroxide were reacted to obtain using the ethyl acetate-hexane mixture (5-5) as eluant for chromatography, 2.5 g of the expected product which was used as is for the following step.

STEP B:
1-methyl-4-[[2-(2-oxirannylmethoxy)-phenyl]-methyl]-1H-indole

Using the procedure of Step A of Example 2, 2.45 g of the product of Step A and 4.05 ml of epichlorhydrin three times were reacted to obtain after chromatography on silica (eluant: methylene chloride), 2.95 g of the desired product melting at 72° C. which was used as is for the following step.

| IR Spectrum: | |
|---|---|
| No OH aromatics: | 1601, 1587, 1514, 1494 cm$^{-1}$ |

STEP C: (±)
1-[(1,1-dimethylethyl)-amino]-3-[2-[(1-methyl-1H-indol-4-yl)-methyl]-phenoxy]-2-propanol and its benzoate Using the procedure of Step F of Example 10, 2.95 g of the epoxide of Step B, 65 ml of ethanol and 6.3 ml of tert-butyl amine were reacted to obtain 5.6 g of the expected product in the form of a base. 3.80 g of the base were dissolved in 70 ml of isopropanol and 1.33 of benzoic acid in solution in 15 ml of isopropanol were added. The mixture was ice-cooled for 12 hours, separated, washed with isopropanol, then with ether and dried at 80° C. under reduced pressure to obtain 2.61 g of the expected product melting 136° C.

Analysis: $C_{23}H_{30}N_2O_2$. $C_7H_6O_2$; Calculated: %C 73.74; %H 7.43 %N 5.73; Found: 73.6; 7.4; 5.7.

EXAMPLE 12

[2-[3-[(1,1-dimethylethyl)-amino]-propoxy]-phenyl]-(1-methyl-1H-indol-4-yl) methanone STEP A:
[2-(3-chloropropoxy)-phenyl](1-methyl-1H-indol-4-yl) methanone A mixture of 8 g of the product of Step D of example 10, 8.80 g of potassium carbonate, 215 ml of acetone and 12.53 ml of 1-bromo -3-chloro-propane was stirred at reflux for 24 hours and the mixture was allowed to return to ambient temperature, then filtered, washed with acetone and concentrated to dryness under reduced pressure. The residue was chromatographed on silica (eluant: methylene chloride - hexane 7-3) to obtain 10.4 g of the desired product melting at 60° C. which was used as is for the following step.

| IR Spectrum | |
|---|---|
| No OH C=O | 1649 cm$^{-1}$ |
| conjugated system + aromatic | 1599, 1582, 1568, 1508 cm$^{-1}$ |

STEP B:
[2-[3-[(1,1-dimethylethyl)-amino]-propoxy]-phenyl]-(1-methyl-1H-indol-4-yl) methanone A mixture of 10.30 g of the product of Step B, 8.68 g of potassium carbonate, 13.13 ml of tert.-butylamine and 180 ml of ethanol was heated at 150° C. for 24 hours in an autoclave. The mixture was filtered and evaporated to dryness under reduced pressure. The residue was chromatographed on silica (eluant: ethyl acetate - triethylamine 95-05) to obtain 11.06 g of the desired product in the form of a base. Then, the operation was carried out as in Step C in Example 11 using 3 g of the above base and 1 g of benzoic acid to obtain 3.15 g of the benzoate melting at 172° C.

Analysis: $C_{23}H_{28}N_2O_2$. $C_7H_6O_2$; Calculated: %C 74.05 %H 7.04 %N 5.76; Found: 74.0; 7.0; 5.8.

EXAMPLE 13

(±)
α-[2-[3-[(1,1dimethylethyl)-amino]-propoxy]-phenyl]-1-methyl-1H-indol-4-methanol and its fumarate STEP A: (±)
α-[2-[3-[(1,1-dimethylethyl)-amino]-propoxy]-phenyl]-1-methyl-1H-indol-4-yl) methanone 0.4 g of [2-[3-[(1,1-dimethylethyl)-amino]-propoxy]-phenyl]-(1H-indol-4-yl) methanone of Step F of Example 3, 8 ml of methylene chloride, 0.07 ml of methyl iodide, 4 ml of 5N sodium hydroxide and 0.39 8 of tetrabutyl ammonium hydrogenosulfate were stirred for 5 hours at ambient temperature. The mixture was diluted with water and extracted with methylene chloride. The organic phase was washed with salt water, dried and evaporated to dryness under reduced pressure. The residue was chromatographed on silica (eluant: ethyl acetate-triethylamine 95-5) to obtain 0.4 g of the expected product melting at 60° C.

STEP B: (±)
α-[2-[3-[(1,1-dimethylethyl)-amino]-propoxy]-phenyl-1-methyl-1H-indol-4-methanol and its fumarate 3.30 g of the product of Step A in 33 ml of butanol in the presence of 1.027 of sodium borohydride was refluxed for 1 hour and was then cooled to ambient temperature and then poured into 100 ml of a saturated aqueous solution of sodium carbonate. The mixture was extracted with ethyl acetate and the extracts were concentrated to dryness under reduced pressure. The residue was chromatographed on silica (eluant: ethyl acetate - triethylamine 95-5) to obtain 3.04 8 of the expected product in the form of the base melting at 124° C. Then the fumarate was prepared as in Step G of Example 1 using 3.4 g of the base and 1.07 R of fumaric acid to obtain 3.48 8 of the expected fumarate melting at 208° C.

Analysis: $C_{23}H_{30}N_2O_2 \cdot C_4H_4O_4$. Calculated: %C 67.2; %H 7.10; %N 5.80; Found: 67.5; 7.2; 5.8.

EXAMPLE 14

1,3-dihydro-4-[2-[3-(1,1-dimethylethyl)-amino]-propoxy]-benzoyl]-2H-indol-2-one and its fumarate

STEP A:
[2-[3-(1,1-dimethylethyl)-amino]-propoxy]-phenyl-(3-chloro-1H-indol-4-yl) methanone 6.3 g of [2-[3-[(1,1-dimethylethyl)-amino]-propoxy]-phenyl]-(1H-indol-4-yl) methanone of Step F of Example 3 in 50 ml of acetic acid in the presence of 2.64 g of N-chloro succinimide was stirred for 2 hours at ambient temperature and was then poured into 300 ml of saturated aqueous solution of sodium carbonate and extracted with ethyl acetate. The organic phase was washed with salt water, dried and concentrated to dryness. After chromatography of the residue on silica (eluant: ethyl acetate triethylamine 95-5), 5.52 g of the expected product were obtained and was used as is for the following step.

STEP B:
1,3-dihydro-4-[2-[3-(1,1-dimethylethyl)-amino]-propoxy]-benzoyl]-2H-indol-2-one and its fumarate 5.50 g of the product of Step A in 77 ml of ethanol in the presence of 154 ml of N hydrochloric acid were refluxed for 90 minutes and the mixture was allowed to return to ambient temperature and then poured into 170 ml of N sodium hydroxide and extracted with ethyl acetate. The organic phase was washed, dried and concentrated to dryness. The 5.7 g of crude product were chromatographed on silica (eluant: ethyl acetate - methanol - triethylamine 8-1-1) and after forming a paste with isopropyl ether and drying under reduced pressure. 3.80 g of the expected product melting at 132° C. were obtained. The fumarate was prepared as in Step G of Example 1 using 2.5 g of the base and 0.79 g of fumaric acid in ethanol to obtain after crystallization, 1.51 g of the expected fumarate melting at 258° C.

Analysis: $C_{22}H_{26}N_2O_3 \cdot C_4H_4O_4$; Calculated: %C 67.91; %H 6.65; %N 6.60; Found: 67.9; 6.6; 6.3.

EXAMPLE 15

1,3-dihydro-4-[2-[3-[(1,1-dimethylethyl)-amino]-2-hydroxypropoxy]-benzoyl]-2H-indol-2-one and its neutral fumarate A solution of 4 g of neutral fumarate of Step C of Example 4, 160 ml of ethanol and 1.57 g of N-chlorosuccinimide was refluxed for 1 hour and the solution was cooled to ambient temperature. 50 ml of N sodium hydroxide and 100 ml of water were added and extraction was done with ethyl acetate. The organic phase was washed with salt water, dried and brought to dryness to obtain 3.6 g of chlorinated intermediate to which 57.6 ml of ethanol and 114 ml of hydrochloric acid were added. The mixture was stirred for 24 hours at ambient temperature, then for 45 minutes at reflux and then allowed to return to ambient temperature. 150 ml of N sodium hydroxide were added, followed by extraction with ethyl acetate. The extracts were dried and concentrated to dryness and the residue was chromatographed on silica (eluant: ethyl acetate-methanol-triethylamine 80-10-10) to obtain 237 g of the expected product in the form of the base melting at 158° C. Then, the operation was carried out as in Step G of Example 1 starting with 2.3 g of the base and 1.46 g of fumaric acid to obtain 1.78 g of the expected product melting at 236° C.

EXAMPLE 16

[2-[2-(1,1-dimethylethyl)-amino]-ethoxy]-phenyl-(1H-indol-4-yl)-methanone and its fumarate

STEP A: [2-(2-chloroethoxy)-phenyl]-(1H-indol-4-yl) methanone 6 g of the product of Step D of Example 3, 192 ml of toluene, 90 ml of acetonitrile, 2.16 g of tetrabutyl ammonium hydrogen sulfate, 9.18 ml of 2-chloroethanol tosylate and 90 ml of 5N sodium hydroxide were stirred for 72 hours at 50° C. The mixture was diluted with water and extracted with ethyl acetate. The organic phase was washed, dried and concentrated to dryness under reduced pressure. The residue was chromatographed on silica (eluant: methylene chloride) to obtain 5.39 g of the desired product which was used as is for the following step.

STEP B:
[2-[2-[(1,1-dimethylethyl)-amino]-ethoxy]-phenyl]-(1H-indol-4-yl) methanone and its fumarate Using the procedure of Step F of Example 1, 5.46 B of the product of Step A, 5.03 g of potassium carbonate and 7.61 ml of terbutylamine in 70 ml of ethanol were reacted to obtain 4.95 g of the expected product in the form of the base melting at 140° C. The fumarate was prepared with 4.73 g of the base and 1.63 g of fumaric acid as in Step G of Example 1 to obtain 3.34 g of the desired fumarate which after crystallization from ethanol melted at 180° C. Analysis: $C_{21}H_{24}N_2O_2 \cdot \frac{1}{2} C_4H_4O_4$; Calculated: %C 70.03; %H 6.64; %N 7.10 Found: 70.3; 6.7; 7.1;

EXAMPLE 17

(±)
[2-[2-hydroxy-3-[1-methylethyl)-amino]-propoxy]-phenyl]-(1H-Indol-4-yl) methanone and its fumarate Using the procedure of Step B of Example 2, 3.7 g of the product of Step A of Example 4 and 6.45 ml of isopropylamine in 45 ml of ethanol were reacted to obtain 3.26 g of the expected product obtained in the form of the base. Using the Step G of Example 1, 3.19 g of the base and 1.05 g of fumaric acid were reacted to obtain 1.62 g of the desired fumarate melting at 193° C.

Analysis: $C_{21}H_{24}N_2O_3 \cdot \frac{1}{2} C_4H_4O_4$; Calculated: %C 67.30; %H 6.38; %N 6.82; Found: 67.4; 6.6; 6.7.

Example 18

(±)
[2-[3-[[bis-1-methylethyl)-amino]-2-hydroxy-propoxy]-phenyl]-(1H-indol-4-yl) methanone and its hydrochloride 1 g of the product of Step A of Example 4 in 40 ml of ethanol were refluxed for 4 hours and 2.4 ml of diisopropylamine were added. The solvent was eliminated under reduced pressure and after the mixture was cooled down to 4° C., a paste was made with ether to obtain 880 mg of the desired product in the form of the base melting at 100° C. 2.1 g of the base were dissolved in 100 ml of ethyl acetate at ambient temperature and 3 ml of a saturated ethyl acetate solution in hydrochloric acid were added, followed by icing for 1 hour, separating and drying under reduced pressure to obtain 2.25 g of the desired hydrochloride melting at 210 to 212° C.

Analysis: $C_{24}H_{30}N_2O_3$. HCl; Calculated: %C 66.89; %H 7.25; %Cl 8.23 %N 6.5 Found: 66.6; 7.4; 8; 6.2.

EXAMPLE 19

(±)
[2-[2-hydroxy-3-(4-methyl-1-piperazinyl)-propoxy]-phenyl]-(1H-indol-4-Yl) methanone and its fumarate Using the procedure of Step B of Example 2, 2.5 g of the product of Step A of Example 4 and 4.73 ml of N-methyl piperazine were reacted to obtain after chromatography on silica (eluant : chloroform-methanol-triethylamine 8-1-1), 3 g of the expected product in the form of the base. Using the procedure G of Example 1, 3.3 g of the base and 0.97 g of fumaric acid were reacted to obtain 3.25 g of the desired fumarate which after crystallization from ethanol melted at 186° C.

Analysis: $C_{23}H_{27}N_3O_3$. ½ $C_4H_4O_4$; Calculated: %C 66.5 %H 6.47, %N 9.31 Found: 66.4; 6.5; 9.3;

EXAMPLE 20

(±)
[2-[2-hydroxy-3-(propylamino)-propoxy]-phenyl]-(1H-indol-4-yl) methanone and its fumarate Using the procedure of Example 19, 3 g of the product of Step A of Example 4 and 5.22 ml of N-propylamine were reacted to obtain 2.4 g of the expected product in the form of the base which was reacted with 0.79 g of fumaric acid to obtain 1.67 g of the expected fumarate melting at 175° C.

Analysis: $C_{21}H_{24}N_2O_3$. ½ $C_4H_4O_4$; Calculated; %C 67.3; %H 6.38; %N 6.82; Found: 67.2; 6.3; 6.8.

EXAMPLE 21

(±)
[2-[(3-cyclohexylamino)-2-hydroxylpropoxy]-phenyl]-(1H-indol-4-yl) methanone Using the procedure of Example 19, 3 g of the product of Step A of Example 4 and 5.8 ml of cyclohexylamine were reacted to obtain 2 g of the expected product in the form of tho base which was crylstallized from acetonitrile to obtain 1.6 g of pure product melting at 136 to 138° C.

Analysis: $C_{24}H_{28}N_2O_3$; Calculated: %C 73.44; %h 7.19; %N 7.14; Found: 73.5; 7.5; 7.2.

EXAMPLE 22

(±)
3-(1,1-dimethylethyl)-amino]-[2-[1-(1H-indol-4-yl)-ethenyl]-phenoxy]-2-propanol and its hydrochloride STEP A: 2-[1-(1H-indol-4-yl)-ethenyl]-phenol Preparation of the methyl magnesium iodide 52 ml of methyl iodide in 400 ml of ether were slowly added to 20 g of magnesium turnings in 70 ml of ether and the mixture was refluxed for 1 hour to obtain the expected magnesium compound titrating 1.48 M/l.

Condensation 20 g of (2-hydroxy phenyl)-(1H-indo-4-yl) methanone of Step D of Example 3 in solution in 400 ml of tetrahydrofuran were added at ambient temperature to 236 ml of a solution of the magnesium compound obtained above. The other was eliminated and replaced with tetrahydrofuran. The mixture was refluxed for 1 hour, cooled down and the excess magnesium compound was destroyed by the addition of a saturated aqueous solution of ammonium chloride. The mixture was diluted with water and extracted with ethyl acetate. The organic phase was dried and the solvents were eliminated under reduced pressure at 50° C. to obtain 21.9 g of crude product which was chromatographed on silica (eluant: methylene chloride - ethyl acetate 98-2) to obtain 17.8 g of the desired product which was crystalized from isopropyl ether to obtain 17.4 g of pure product in two lots melting at 117 to 118° C.

STEP B:
4-[1-[2-[(2-oxyrannyl)-methoxy]-phenyl]-ethenyl]-1H-indole

Using the procedure of Step A of Example 2, 7 g of the product of Step A, 4.2 g of potassium carbonate and 24 ml of epichlorhydrin added iu two lots. After a total of 44 hours of reflux, the mixture was filtered and concentrated to dryness under reduced pressure at 50° C. The residue was chromatographed on silica (eluant: methylene chloride - ethyl acetate 98-2) to obtain 7.35 g of the expected product which after crystallization from isopropyl ether melted at 87 to 88° C.

STEP C: (±)
3-[(1,1-dimethylethyl)-amino]-1-[2-[1-(1H-indol-4-yl)-ethenyl]-phenoxy]-2-propanol and its hydrochloride Using the procedure of Step B of Example 2, 7 g of the product of Step B, 70 ml of and 35 ml of tert-butylamine were reacted to obtain 7.7 g of the desired product in the Form of the base melting at 127 to 128° C.

| IR Spectrum: (CHCl$_3$) | |
| --- | --- |
| OH | 3535 cm$^{-1}$ |
| =C—NH | 3490 cm$^{-1}$ |
| C=C + aromatic | 1620, 1600, 1580, 1490 cm$^{-1}$ |

3.7 g of the base were dissolved at ambient temperature in 200 ml of ethyl acetate and the hydrochloride was formed by the addition of a solution of hydrochloric acid in ethyl acetate to obtain 2.7 g of the expected hydrochloride which after crystallization from ethanol melted at 204 to 205° C.

Analysis: $C_{23}H_{28}N_2O_2$. HCl Calculated: %C 68.90; %H 7.29; %Cl 8.84; %N 6.99; Found: 69.1; 7.5; 8.8; 6.8.

EXAMPLE 23

(±) 3-[(1,1-dimethylethyl)-amino]-1-[2-[1-(1H-indol-4-yl)-ethyl]-phenoxy]-2-propanol and its hydrochloride 4.1 g of the base of Step C of Example 22 in 400 ml of ethanol were hydrogenated for 30 minutes at 50° C. in the presence of 1.3 B of activated charcoal with 10% palladium and the catalyst was filtered. The solvent was eliminated at 50° C. under reduced pressure to obtain 4.6 g of crude product which was crystallized from isopropyl ether to obtain 3.3 g of the expected product in the form of the base melting at 135 to 137° C.

| IR Spectrum: (CHCl$_3$) | |
| --- | --- |
| OH | approx. 3630 cm$^{-1}$ |
| =C—NH | approx. 3486 cm$^{-1}$ |
| C=C + aromatic | approx. 1610, 1599, 1586, 1492 cm$^{-1}$ |

3.3 g of the base were dissolved in 400 ml of isopropyl ether and the hydrochloride was formed by the addition of a saturated solution of hydrochloric acid in acetonitrile to obtain 2.6 g of the desired hydrochloride melting at 208 to 209° C.

Analysis: $C_{23}H_{30}N_2O_2 \cdot CHl$; Calculated: %C 68.56; %H 7.75; %Cl 8.80; %N 6.95; Found: 68.3; 7.9; 8.8; 7.0.

EXAMPLE 24

N-(1,1-dimethylethyl)-3-[2-[1-(1H-indol-4-yl)-ethenyl]-phenoxy]-propanamide and its hydrochloride

STEP A:
4-[1-[2-(3-chloropropoxy)-phenyl]-ethenyl]-1H-indole

Using the procedure of Step E of Example 1, 6.7 g of 2-[1-(1H-indol-4-yl)-ethenyl]-phenol of Step A of Example 22, 70 ml of acetone, 4 g of potassium carbonate and 11.5 ml of 1-chloro-3-bromo-propane were heated for 20 hours at reflux and after Chromatography and crystallization from petroleum ether (Eb=40-70° C.), 7.05 g of the desired product melting at 70 to 72° C. were obtained.

STEP B:
N-(1,1-dimethylethyl)-3-[2-[1-1H-indol-4-yl)-ethenyl]-phenoxy]-propanamide and its hydrochloride Using the procedure of Step F of Example 1, with heating for 6 hours at 120° C., 70 g of the product of Step A, 50 ml of tert-butylamine and 2.9 g of potassium carbonate in 50 ml of ethanol were reacted to obtain after chromatography and crystallization from isopropyl ether, 7.4 g of the expected product in the form of the base melting at 112° C.

| IR Spectrum: (Nujol) | |
| --- | --- |
| NH indole | 3630 cm$^{-1}$ |
| C=C, C=N and aromatic | approx. 1615, 1597, 1578 cm$^{-1}$ |

The hydrochloride was prepared as in Step C of Example 22 using 4.6 g of the base to obtain 3.35 g of the expected hydrochloride melting at 238 to 240° C.

Analysis: $C_{23}H_{28}N_2O \cdot HCl$; Calculated: %C 71.76; %H 7.59; %Cl 9.21; %N 7.28; Found: 71.8; 7.6; 9.4; 7.0.

EXAMPLE 25

(±) O-methyloxime of [2-[3-[(2,2-dimethylethyl)-amino]-2-hydroxypropoxy]-phenyl]-(1H-indol-4-yl) methanone and its hydrochloride

STEP A: (±) O-methyloxime of (2-hydroxyphenyl)-(1H-indol-4-yl) methanone 4.8 B of (2-hydroxyphenyl)-(1H-indol-4-yl) methanone of Step D of Example 3 in 100 ml of methanol, 8.5 g of methylhydroxyamine hydrochloride and 4.8 g of sodium acetate in 40 ml of distilled water were refluxed for 7 hours and the methanol was eliminated under reduced pressure. Dilution with water followed by extraction with ethyl acetate and concentration to dryness yielded a residue Which was chromatographed on Silica (eluant: methylene chloride - ethyl acetate 98-2) to obtain 4.08 g of isomer A (M.p.=228° C.) (corresponding to the product crystallized from the chromatography mixture and from the fraction with Rf=0.50) and 900 mg of isomer B (corresponding to the fraction with Rf=0.25).

| Analysis: $C_{16}H_{14}N_2O_2$ | | | |
| --- | --- | --- | --- |
| Calculated: | % C 72.17 | % H 5.30 | % N 10.52 |
| Found | | | |
| Isomer A: | 72.2 | 5.1 | 10.4 |
| Isomer B: | 72.4 | 5.3 | 10.3 |

STEP B: O-methyloxime of [2-(2-oxirannylmethoxy)-phenyl]-(1H-indol-4-yl) methanone Using the procedure of Step A of Example 2, 3.57 g of the product of Step A and 7.5 g of potassium carbonate and 5.4 ml of epichlorhydrine added in four lots were reacted. After a total of 96 hours of reflux, filtering took place, followed by concentrating to dryness. The residue was chromatographed on silica (eluant: hexane-ethyl acetate 7-3) to obtain 2.7 g of expected product melting at 140° C.

STEP C: (±) O-methyloxime of [2-[3-[(2,2-dimethylethyl)-amino]-2-hydroxypropoxy]-phenyl-(1H-indol-4-yl) methanone and its hydrochloride 2.7 g of the product of Step A in 270 ml of ethanol in the presence of 4.42 ml of tert.-butylamine were refluxed for 5 hours and the mixture was cooled down to ambient temperature and concentrated to dryness. The residue was chromatographed on silica (eluant: chloroform-methanol - triethylamine 90-5-5) to obtain 2 g of crude product which was made into a paste with ether to obtain 1.67 B of the desired product in the form of the base melting at 153 to 155° C.

| IR Spectrum: (CHCl$_3$) | |
| --- | --- |
| —OH | 3542 cm$^{-1}$ |
| =C—NH | 3480 cm$^{-1}$ |
| C=N + aromatic | 1610, 1600, 1589 cm$^{-1}$ |

The hydrochloride was prepared as in Step C of Example 22 using 1.7 g of the base and after crystallization from isopropanol, 1.4 g of the expected hydrochloride melting at 246 to 248° C. were obtained.

Analysis: $C_{23}H_{29}N_3O_3 \cdot HCl$; Calculated: %C 63.95; %H 7.00; %Cl 8.21 %N 9.73; Found: 63.7; 7.1; 8.1; 9.6.

EXAMPLE 26

Tablets were prepared containing 100 mg of product of Example 4 and sufficient excipient of: lactose, starch, talc, magnesium stearate for a tablet of 150 mg.

PHARACOLOGICAL STUDY

1) Anti-Arhythmic Acion in the Rat

Male rats weighing 300–350 g, anaesthetized by intraperitoneal route with 1.20 g/kB of urethane, were tracheotomizod and subjected to artificial respiration (40–50 insufflations of 3 ml/minute). Needles were implanted under the skin to record the electrocardiogram of the rats on reception of the DII signal. The test products were administered intravenously or orally. After five minutes in the case of intravenous administration and one hour in the case of oral administration, the jugular vein of the rats was perfused with 10 micrograms/minutes under 0.21 ml of an aconitine solution and the time taken for the first ventricular extrasysloles to appear was noted. The amount of aconitine perfused was calculated, then expressed as a function of the body weight of the animal.

The percentage increase in the aconitine dose necessary to initiate the ventricular extrasystoles after treatment was calculated relative to the control animals. The results which appear in the table hereafter show that the products of the present Application are endowed with remarkable anti-arhythmic properties.

| Product of Example | Route | Dose mg/kg | Percentage protection |
|---|---|---|---|
| 4 | IV | 5 | >217 |
|   | PO | 25 | 73 |
| 9 | IV | 5 | >165 |
|   | PO | 25 | 91 |
| 7 | IV | 5 | >201 |
| 3 | IV | 5 | 202 |
|   | PO | 25 | 52 |
| 2 | IV | 5 | 93 |
|   | PO | 25 | 82 |
| 10 | IV | 1 | 133 |
|   | PO | 25 | 124 |
| 11 | IV | 5 | 257 |
|   | PO | 25 | 81 |
| 12 | IV | 1 | 99 |
| 13 | IV | 5 | 140 |
| 22 | IV | 5 | 84 |
|   | PO | 25 | 33 |
| 23 | IV | 5 | 88 |
| 18 | IV | 5 | 135 |
| 19 | IV | 5 | 142 |
| 21 | IV | 5 | 124 |
| 25 | IV | 5 | 186 |

2) Test for anti-calcic activity in vitro

Isolated caudal artery of the rat.

Caudal artery rings of Wistar rats were suspended in a solution of Krebs-bicarbonate (NaCl: 120.8 mM, XCl: 5.9 mM, Mg $Cl_2$: 1.2 mM, $NaH_2PO_4$: 1.2 mM, $NaHCO_3$: 15.5 mM, glucose: 12.6 mM) without calcium in the presence of phentolamine $10^{-5}$ M oxygenated with a gaseous mixture containing 5% of $CO_2$ in oxygen and maintained at 37° C. After 30 minutes in equilibrium, the preparations were contracted every 15 minutes using a depolarizing solution (NaCl: 26.7 mM, KCl: 100 mM, $MgCl_2$: 1.2 mM, $NaH_2PO_4$: 1.2 mM, $NaHCO_3$: 15.5 mM, glucose: 12.6 mM) containing 2.5 mM of $CaCl_2$. When the contractile responses became reproducible, the test product was added in increasing concentrations 15 minutes before each contraction. The concentration which inhibited by 50% the contraction induced by calcium chloride was calculated ($IC_{50}$). It is noted from the results which appear in the table hereafter that the products o( the present Application possess a strong anti-calcic activity.

| Product of Example | $IC_{50}$ in micromoles |
|---|---|
| 6 | 0.4 |
| 1 | 0.46 |
| 2 | 1.9 |
| 5 | 2 |
| 4 | 6.2 |
| 3 | 1.9 |
| 11 | 3 |
| 12 | 4.8 |
| 16 | 1.1 |
| 22 | 3.8 |
| 23 | 4.7 |
| 24 | 3.1 |
| 18 | 7.2 |

3) Test for the Activity of Anti-Aggregation of Blood Platelets. Blood-Platelet Aggregation, In Vitro, on Plasma Rich in Blood-Platelets (PRP)

Measurement of blood-platelet aggregation was made according to the terbidimetric method of Born et al 1963, J. Physiol., Vol. 168, p. 178. Rabbit's blood was removed on Na citrate at 3.2% of cardiac puncture and the plasma rich in blood-platelets was obtained by centrifuging and adjustment of the number of Blood-platelets to 300,000 per ml. The aggregation was induced by collagen (40 micrograms per ml of PRP) or PAF acether (0.05 micromoles per liter of PRP). The test compounds were incubated at different concentrations in the PRP 2 minutes before the aggregating agent. The results are expressed in $IC_{50}$ (concentration inhibiting the aggregation by 50% relative to the control curves).

| Product of Example | $IC_{50}$ in $10^{-5}$M | |
|---|---|---|
| | Induction by COLLAGEN | Induction by PAF ACETHER |
| 3 | 3.1 | 4.7 |
| 4 | 0.95 | 5.5 |
| 5 | 1.8 | 4.2 |
| 6 | 1.4 | 3.7 |
| 10 | 2.1 | 7 |
| 11 | 1 | 2.4 |
| 12 | 4 | 4 |
| 13 | 6 | 7 |
| 16 | 5.7 | 10 |
| 22 | 0.9 | 1.4 |
| 23 | 0.8 | 2.5 |
| 24 | 0.8 | 1.4 |

4) Study of the Acute Toxicity

The lethal doses $LD_O$ of the various compounds tested were evaluated after oral administration to a mouse. The maximum dose which did not cause any deaths over 8 days was the following results were obtained:

| Product of Example | $LD_0$ in mg/kg |
|---|---|
| 3 | 100 |

-continued

| Product of Example | LD$_0$ in mg/kg |
|---|---|
| 5 | >200 |
| 7 | 100 |
| 8 | >200 |
| 9 | >200 |
| 15 | >200 |
| 22 | 200 |

Various modifications of the compounds and method of the invention may be made without departing from the spirit or scope thereof and it is to be understood that the invention is tended to be limited only as defined in the appended claims,

What we claim is:

1. A compound selected from the group consisting of racemic or diastereoisomer forms of a 4-benzyl-1H-indole compound of the formula

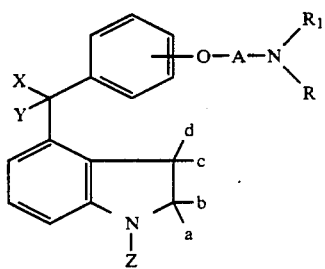

wherein R$_1$ and R taken together with the nitrogen to which they are attached form morpholino or piperazinyl optionally substituted with at least one member of the group consisting of alkyl of 1 to 5 carbon atoms, cycloalkyl of 3 to 7 carbon atoms, cycloalkylalkyl of 4 to 12 carbon atoms, phenyl, naphthyl, aralkyl and diaralkyl of 7 to 14 carbon atoms, A is

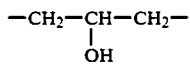

or —(CH$_2$)$_n$, n is 2, 3, 4 or 5, X and Y are both hydrogen or one is hydrogen and the other is selected from the group consisting of —OH, alkoxy and alkyl of 1 to 4 carbon atoms, or X and Y together form a member of the group consisting of ═O, alkylidene of 1 to 4 carbon atoms, a, b, c and d are all hydrogen or a and b form ═O and c and d are hydrogen or one of a and b with one of c and d form a carbon-carbon bond and the others are both hydrogen, Z is selected from the group consisting of hydrogen, alkyl of 1 to 5 carbon atoms, alkenyl and alkynyl of 2 to 5 carbon atoms, cycloalkylalkyl of 4 to 12 carbon atoms and aralkyl of 7 to 14 carbon atoms, all optionally substituted with at least one member of the group consisting of —OH, halogen and alkyl and alkoxy of 1 to 5 carbon atoms and

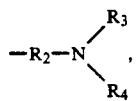

R$_2$ is alkylene of 2 to 5 carbon atoms, R$_3$ and R$_4$ are individually selected from the group consisting of hydrogen, alkyl of 1 to 5 carbon atoms, cycloalkyl of 3 to 7 carbon atoms, cycloalkylalkyl of 4 to 12 carbon atoms and aralkyl of 7 to 12 carbon atoms, all optionally substituted with at least one substituent selected from the group consisting of halogen, alkyl or alkoxy of 1 to 5 carbon atoms, hydroxy, trifluoromethyl, methylthio, nitro, amino and monoalkylamino or dialkylamino where in alkyl of 1–5 carbon atoms or taken together with the nitrogen to which they are attached form morpholino or piperazinyl optionally substituted with at least one member of the group consisting of alkyl of 1 to 5 carbon atoms, cycloalkyl of 3 to 7 carbon atoms, cycloalkylalkyl of 4 to 12 carbon atoms, phenyl, naphthyl and aralkyl and diaralkyl of 7 to 14 carbon atoms or its non-toxic, pharmaceutically acceptable acid addition salts.

2. A compound of claim 1 wherein Z is hydrogen or alkyl of 1 to 4 carbon atoms.

3. A compound of claim 1 wherein X and Y are both hydrogen or together are ═O or alkylidene.

4. A compound of claim 1 wherein A is

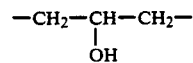

or —(CH$_2$)$_n$— and n is 2 or 3.

5. A compound of claim 1 wherein a and b are ═O and c and d are hydrogen or one of a and b together with one of c and d form a carbon-carbon bond and the other two are hydrogen.

6. A compound of claim 1 wherein is (±) [2-[2-hydroxy-3-(4-methyl-1-piperazinyl)-propoxy]-phenyl]-(1H-indol-4-yl)-methanone and its non-toxic, pharmaceutically acceptable acid addition salts.

7. An antiarhythmic composition comprising an antiarhythmically effective amount of at least one compound of claim 1 and an inert pharmaceutical carrier.

8. A composition of claim 7 wherein in the active compound Z is hydrogen or alkyl of 1 to 4 carbon atoms.

9. A composition of claim 7 wherein in the active compound X and Y are both hydrogen or together are ═O or alkylidene.

10. A composition of claim 7 wherein in A is

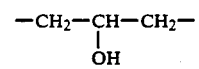

or (CH$_2$)$_n$— and n is 2 or 3.

11. A composition of claim 7 wherein in the active compound a and b are ═O and c and d are hydrogen or one of a and b together with one of c and d form a carbon-carbon bond and the other two are hydrogen.

12. A composition of claim 7 wherein the compound is (±) [2-[2-hydroxy-3-(4-methyl-1-piperazinyl)-propoxy]-phenyl]-(1H-indol-4-yl)-methanone and its non-toxic, pharmaceutically acceptable acid addition salts.

13. A method of inducing antiarhythmic activity in warm-blooded animals comprising administering to warm-blooded animals an antiarhythmically effective amount of at least one compound of claim 1.

14. A method of claim 13 wherein in the active compound Z is selected from the group consisting of hydrogen, alkyl of 1 to 5 carbon atoms, alkenyl and alkynyl of 2 to 5 carbon atoms, cycloalkylalkyl of 4 to 7 carbon atoms, aralkyl of 7 to 14 carbon atoms optionally having 1 to 3 substituents selected from the group consisting of —OH, halogen, and alkyl and alkoxy of 1 to 5 carbon atoms and

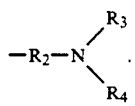

wherein $R_3$ and $R_4$ are individually selected from the group consisting of hydrogen and alkyl of 1 to 5 carbon atoms and $R_2$ is alkylene of 2 to 5 carbon atoms.

15. A method of claim 13 wherein Z is hydrogen or alkyl of 1 to 4 carbon atoms.

16. A method of claim 13 wherein X and Y are both hydrogen or together are =O or alkylidene.

17. A method of claim 13 wherein A is

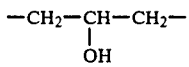

or —$(CH_2)_n$— and n is 2 or 3. carbon atoms.

18. A method of claim 13 wherein a and b are =O and c and d are hydrogen or one of a and b together with one of c and d form a carbon-carbon bond and the other two are hydrogen.

19. A method of claim 13 wherein the compound is (±) [2-[2-hydroxy-3-(4-methyl-1-piperazinyl)-propoxy]-phenyl]-(1H-indol-4-yl)-methanone and its non-toxic, pharmaceutically acceptable acid addition salts.

* * * * *